(12) United States Patent
Behrens et al.

(10) Patent No.: US 10,113,893 B2
(45) Date of Patent: Oct. 30, 2018

(54) METHOD OF, AND APPARATUS FOR, MONITORING THE AVAILABLE RESOURCES OF A GAS CYLINDER

(71) Applicants: Marcel Behrens, Vilvoorde (BE); Gareth Ross Pemberton, Worcester (GB)

(72) Inventors: Marcel Behrens, Vilvoorde (BE); Gareth Ross Pemberton, Worcester (GB)

(73) Assignee: Air Products and Chemicals, Inc., Allentown, PA (US)

( * ) Notice: Subject to any disclaimer, the term of this patent is extended or adjusted under 35 U.S.C. 154(b) by 308 days.

(21) Appl. No.: 15/021,324

(22) PCT Filed: Sep. 12, 2014

(86) PCT No.: PCT/EP2014/069548
§ 371 (c)(1),
(2) Date: Mar. 11, 2016

(87) PCT Pub. No.: WO2015/036569
PCT Pub. Date: Mar. 19, 2015

(65) Prior Publication Data
US 2016/0223377 A1    Aug. 4, 2016

(30) Foreign Application Priority Data

Sep. 13, 2013 (EP) .................................. 13184383

(51) Int. Cl.
*G01F 1/86* (2006.01)
*G01G 17/04* (2006.01)
*G01G 3/16* (2006.01)
*G01N 9/00* (2006.01)

(52) U.S. Cl.
CPC ............... *G01F 1/86* (2013.01); *G01G 17/04* (2013.01); *G01G 3/16* (2013.01); *G01N 9/002* (2013.01)

(58) Field of Classification Search
CPC .......................................................... G01F 1/86
See application file for complete search history.

(56) References Cited

FOREIGN PATENT DOCUMENTS

| DE | 102005004319 A1 | 8/2006 |
|---|---|---|
| EP | 2365297 A1 | 9/2011 |
| EP | 2458344 A1 | 5/2012 |

(Continued)

OTHER PUBLICATIONS

European Patent Office, International Search Report of the International Searching Authority, dated Nov. 28, 2014, for PCT/EP2014/069548.

*Primary Examiner* — Yu-Hsi D Sun
(74) *Attorney, Agent, or Firm* — Larry S. Zelson

(57) ABSTRACT

A method of determining the predicted usage of gas from a gas cylinder and valve assembly. The method comprises determining, using a sensor assembly and at a time t, the mass of gas in the gas cylinder, the average flow rate of gas from the gas cylinder; and the time remaining until the quantity of gas in the gas cylinder reaches a predetermined level, the time remaining being determined, at time t, from the mass of gas in the gas cylinder, the average flow rate of gas from the gas cylinder, and a predetermined scaling factor selected in dependence upon the proportion of gas remaining in the gas cylinder. The average flow rate is determined based on previous measurements, and the amount of gas remaining in the gas cylinder.

16 Claims, 10 Drawing Sheets

(56) References Cited

FOREIGN PATENT DOCUMENTS

| | | |
|---|---|---|
| EP | 2667176 A1 | 11/2013 |
| JP | 2001074532 | 3/2001 |
| JP | 2006183685 | 7/2006 |
| JP | 2007047125 | 2/2007 |
| JP | 2007255666 | 10/2007 |
| JP | 2007309778 | 11/2007 |
| JP | 2008026099 | 2/2008 |
| WO | 2012014375 A1 | 2/2012 |

METHOD OF, AND APPARATUS FOR, MONITORING THE AVAILABLE RESOURCES OF A GAS CYLINDER

The present invention relates a method of determining the predicted usage of gas from a gas cylinder and valve assembly. More particularly, the present invention relates to a method of determining the predicted usage of gas from a gas cylinder using a piezoelectric oscillator immersed in the gas within the gas cylinder.

A compressed gas cylinder is a pressure vessel designed to contain gases at high pressures, i.e. at pressures significantly greater than atmospheric pressure. Compressed gas cylinders are used in a wide range of markets, from the low cost general industrial market, through the medical market, to higher cost applications, such as electronics manufacture utilising high purity corrosive, toxic or pyrophoric speciality gases. Commonly, pressurised gas containers comprise steel, aluminium or composites and are capable of storing compressed, liquefied or dissolved gases with a maximum filling pressure up to 450 barg (where barg is a measure of the pressure (in bar) above atmospheric pressure) for most gases, and up to 900 barg for gases such as hydrogen and helium.

The present invention is particularly applicable to permanent gases. Permanent gases are gases which cannot be liquefied by pressure alone, and for example can be supplied in cylinders at pressures up to 450 bar g. Examples are Argon and Nitrogen. However, this is not to be taken as limiting and the term gas may be considered to encompass a wider range of gases, for example, both a permanent gas and a vapour of a liquefied gas. Vapours of liquefied gases are present above the liquid in a compressed gas cylinder. Gases which liquefy under pressure as they are compressed for filling into a cylinder are not permanent gases and are more accurately described as liquefied gases under pressure or as vapours of liquefied gases. As an example, nitrous oxide is supplied in a cylinder in liquid form, with an equilibrium vapour pressure of 44 barg at 15° C. Such vapours are not permanent or true gases as they are liquefiable by pressure or temperature around ambient conditions.

In many instances, it is necessary to monitor the contents of a given cylinder or pressure vessel to determine the amount of gas remaining. This is particularly critical in situations such as health care applications.

It is known to calculate, in accordance with the gas laws, the variation in contents of a cylinder from knowledge of the pressure of gas within a cylinder. Pressure measurement is a well known art and there are a variety of devices which function to measure pressure. The most conventional type uses an elastic diaphragm equipped with strain gauge elements. However, although one of the lowest cost pressure sensors currently made, these sensors tend to be relatively large in size, and have a mechanical structure which although producible by mass-production photolithographic methods is still relatively complex and expensive to make. They also have a certain degree of fragility and require calibration and temperature compensation before they can be used.

A known arrangement is shown in EP 2 458 344 which relates to the measurement of the true contents of a gas cylinder using a piezoelectric crystal oscillator arranged to measure mass contents of a gas cylinder. In general, a simple measurement of the change in mass contents over time can be used to provide an indication of time for which a gas cylinder can continue to provide a particular flow rate.

However, in general, such an approximation is insufficiently accurate for most applications. Consider, for example, shielding gas flow for MIG/MAG and TIG welding applications. Similar situations may well apply equally to other gas applications supplied by high pressure gas cylinders, such as in food MAP, beverage dispensing systems and medical applications.

Gases stored at significantly high pressure do not follow the laws of an ideal gas; in reality the compressibility of gas and the effects of the ambient temperature must be accounted for in order to determine content. It is thus that a basic calculation of usage time from pressure and flow rate will not give an accurate and reliable answer to the user.

Further, when gases are mixed their compressibility and response to temperature variations alters as the molecular weight of the mixture changes while components are added and mixed.

In addition, the use of a high pressure gas cylinder requires a regulator to reduce the pressure close to the application use pressure, for instance just above atmospheric for welding. The use of a regulator determines that each time the cylinder is used, a surge of gas is experienced by the user.

FIG. 1 shows a conventional arrangement for MIG/MAG welding. A gas cylinder assembly 10 is arranged to store gas at high pressure, for example, 200 to 300 bar. The gas cylinder assembly 10 has a gas cylinder 12 comprising a generally cylindrical container having a flat base arranged to enable the gas cylinder 12 to stand unsupported on a flat surface.

The gas cylinder 12 is formed from steel, aluminium and/or composite materials and is adapted and arranged to withstand the significant internal pressures resulting from the storage of high pressure gas.

A primary regulator 14 is located downstream of the gas cylinder 12, the primary regulator 14 comprising a control valve employing a feedback mechanism such that a constant pressure is maintained at a point downstream of the primary regulator 14. A safety relief valve 16 is arranged downstream of the pressure regulator 14. The regulator 14 supplies gas at a fixed pressure to MIG/MAG welding equipment 18 connected thereto.

The flow rate is generally controlled by restricting the gas flow, typically through valves or orifices. Gas flow can be precisely metered by controlling the upstream pressure across a fixed orifice size, where the downstream pressure is substantially lower than the upstream pressure.

Consider, for example, welding applications equipment such as shown in FIG. 1. In such arrangements, the pressure through hoses and pipework in the welding machinery leading to the welding torch is significantly lower than the upstream pressure in a cylinder. Therefore, in such cases, an orifice located close to the pressure source can function as the principle restriction, with the flow rate being determined by the pressure just upstream of the orifice.

However, if the flow is stopped at the end of the hose and pipework, for example, by a solenoid on/off valve linked to weld arc control, then the pressure will rise in the system downstream of the orifice until it equals the pressure upstream. This rise in system pressure between flowing (dynamic) and static conditions can cause undesirable effects.

The above problems combine, in use, to give rise to 'surge' behaviour. A surge is a phenomenon which occurs when a gas changes from static to flowing conditions, for example when a final closure valve is opened.

Upon opening a valve, there is a transition time between first starting gas flow and achieving a steady state condition.

During this time, the pressure in the applications equipment reduces from the static pressure in storage (which is equal to the upstream pressure) to a much reduced level close to atmospheric pressure. Due to this pressure gradient, the flow rate will be higher, leading to higher gas use than may be necessary for a brief, but significant, amount of time.

Further, the operational duty cycle (i.e. the time for which the gas is flowing relative to time for which the gas feed is closed) can also affect the surge volume. Rapid on/off cycling, for example as necessary in tack welding application can require the proportion of off time to be similar to the proportion of "on" time, leading to significant surge issues.

FIG. 2 is a graph illustrating this phenomenon. It can be seen from this figure that the flow rate never settles to a steady-state, constant flow condition (such as when a valve is always open) before the flow is stopped in the duty cycle. As can be seen, the surge can cause a greater volume of gas to be emitted briefly than is required. The surge phenomenon can cause a simple extrapolation time to run meter to grossly over-read because it is not accounted for in a simple calculation of content and flow.

Surge is just one example of non-linear gas flow behaviour which can cause a straightforward time to run calculation to be grossly inaccurate. However, numerous other issues can cause inaccuracy in the measurement of time to run out of the gas flow. For many applications, such as healthcare uses, such errors may be entirely unacceptable and potentially hazardous.

In summary, simple calculations to predict the time left to use a cylinder cannot be used for critical applications. Nor can the time a cylinder has been in use verify the usage rate (flow-rate) for quality inspections.

Therefore, known measuring arrangements suffer from a technical problem that they are unable to provide accurate measurement of the time remaining until the contents of a gas cylinder are used or reach a critically low level.

According to an embodiment of the present invention, there is provided a method of determining the predicted usage of gas from a gas cylinder and valve assembly using a sensor assembly comprising a gas sensor, the method comprising: a) determining, using the gas sensor, the mass of gas in the gas cylinder at a time t; b) determining, at time t, the average flow rate of gas from the gas cylinder; and c) determining, at time t, the time remaining until the quantity of gas in the gas cylinder reaches a predetermined level, the time remaining being determined from the mass of gas in the gas cylinder at time t, the average flow rate of gas from the gas cylinder at time t, and a predetermined scaling factor selected in dependence upon the proportion of gas remaining in the gas cylinder at time t.

According to a first aspect of the present invention, there is provided a method of determining the predicted usage of gas from a gas cylinder assembly comprising a gas cylinder and a valve and regulator assembly, the method using a sensor assembly comprising a gas sensor and comprising the steps of: a) determining, using the gas sensor, the mass of gas in the gas cylinder at a time t; b) determining, at time t, the average measured flow rate of gas from the gas cylinder; and c) determining, at time t, the time remaining until the quantity of gas in the gas cylinder reaches a predetermined level, the time remaining being determined from the mass of gas in the gas cylinder at time t, the average measured flow rate of gas from the gas cylinder as determined at time t, and a predetermined scaling factor selected in dependence upon the proportion of gas remaining in the gas cylinder at time t.

By providing such a method, the average flow rate is determined based on previous measurements, and this is combined with a factor dependent upon the amount of gas remaining in the gas cylinder. The inventors of the present invention have found that the behaviour of gas flow output from a gas cylinder is dependent upon the proportion of gas remaining in the gas cylinder, i.e. upon the fill level of the gas cylinder. Therefore, the proportion of gas remaining (which may be expressed as a percentage of the maximum fill level) is used as a factor in calculating the time to run of the gas cylinder. Such a method enables a more accurate determination of the available time before the quantity of gas in the gas cylinder reaches a predetermined level (e.g. empty, 10% or any other suitable value).

In an embodiment, the gas sensor comprises a piezoelectric oscillator immersed in the gas within the gas cylinder, and the sensor assembly comprises a drive circuit for driving the piezoelectric oscillator, and step a) comprises: d) driving, by means of the drive circuit, the piezoelectric oscillator such that the piezoelectric oscillator resonates at a resonant frequency; and e) measuring the resonant frequency of the piezoelectric oscillator at time t; and f) determining, from the resonant frequency, the mass of the gas within the gas cylinder at time t.

In an embodiment, step b) comprises determining the average flow rate of gas from either: g) n previous measurements of the flow rate of the gas, where n>1; or h) where there are fewer than n previous measurements of the flow rate of the gas, a predetermined starting flow rate.

In an embodiment, each of said previous measurements of the flow rate of the gas is calculated from the difference between the resonant frequency of the piezoelectric oscillator at a first time and the resonant frequency of the piezoelectric oscillator at a second, earlier, time.

In an embodiment, the method further comprises prior to step a): i) determining the mass of gas in the gas cylinder when the gas cylinder is full, and wherein step c) further comprises: j) determining the proportion of gas remaining in the gas cylinder at time t from the mass of gas in the gas cylinder when full and the mass of the gas in the gas cylinder at time t.

In an embodiment, the predetermined scaling factor is selected from a look up table.

In an embodiment, the time remaining until a predetermined quantity of gas remains in the gas cylinder is calculated based on a first function dependent upon a constant base flow rate and a second function based on the average flow rate of gas.

In an embodiment, the constant base flow rate comprises a predetermined fixed value. In an embodiment, the constant base flow rate is selected from a plurality of constant base flow rates stored in a look up table. In an embodiment, the constant base flow rate is selected by a user.

In an embodiment, the time remaining until a predetermined quantity of gas remains in the gas cylinder is calculated based on a function comprising a constant base flow rate and the average measured flow rate of gas.

In an embodiment, the relative weight of the constant base flow rate component to the average measured flow rate component in the calculation is dependent upon the predetermined scaling factor.

In an embodiment, the method further comprises the step of: k) updating the constant base flow rate based on a measurement of the actual flow rate.

In an embodiment, the updating in step k) is carried out every l measurements of the flow rate. In an embodiment, l is in the range of five to fifteen.

In an embodiment, the relative proportion of the first function and second function in the calculation is dependent upon the predetermined scaling factor.

In an embodiment, the predetermined level of the quantity of gas in the gas cylinder is substantially zero. In an embodiment, the predetermined level of the quantity of gas in the gas cylinder is approximately ten percent of the quantity of gas in the gas cylinder when the gas cylinder is full.

According to an aspect of the present invention, there is provided a sensor assembly comprising a processor and a gas sensor arranged, in use, to be contact with the gas from the gas cylinder, the sensor assembly being configured to determine, using the gas sensor, the mass of gas in the gas cylinder at a time t, to determine, at time t, the average flow rate of gas from the gas cylinder, and to determine, at time t, the time remaining until the quantity of gas in the gas cylinder reaches a predetermined level, the processor being operable to determine the time remaining from the mass of gas in the gas cylinder at time t, the average flow rate of gas from the gas cylinder at time t, and a predetermined scaling factor selected in dependence upon the proportion of gas remaining in the gas cylinder at time t.

In one embodiment, the gas sensor comprises a piezoelectric oscillator, the sensor assembly comprising a drive circuit for driving the piezoelectric oscillator at a resonant frequency.

According to a second aspect of the present invention, there is provided a sensor assembly comprising a processor and a gas sensor, the sensor assembly being configured to carry out the steps of the first aspect.

In one embodiment, the gas sensor comprises a piezoelectric oscillator for immersion in the gas within the gas cylinder and the sensor assembly further includes a drive circuit for driving the piezoelectric oscillator at a resonant frequency.

According to a second aspect of the present invention, there is provided a sensor assembly comprising a processor, a piezoelectric oscillator for immersion in the gas within the gas cylinder and a drive circuit for driving the piezoelectric oscillator at a resonant frequency, the processor being configured to carry out the steps of the first aspect.

In an embodiment, the sensor assembly further comprises a display arranged to be located on the gas cylinder and valve assembly.

In an embodiment, the sensor assembly further comprises wireless communication means for communicating with external electronic devices.

According to an aspect of the present invention, there is provided a gas cylinder and valve arrangement comprising the sensor assembly of the second aspect.

According to a third aspect of the present invention, there is provided a gas cylinder assembly comprising a and valve and regulator arrangement assembly comprising and the sensor assembly of the second aspect.

According to a fourth aspect of the present invention, there is provided a computer program product executable by a programmable processing apparatus, comprising one or more software portions for performing the steps of the first aspect.

According to a fifth aspect of the present invention, there is provided a computer usable storage medium having a computer program product according to the fourth aspect stored thereon.

Embodiments of the present invention will now be described in detail with reference to the accompanying drawings, in which.

The present invention provides a method of, and sensor arrangement for, predicting the time to run from a gas cylinder. A gas cylinder arrangement suitable for use with the present invention will now be described.

Figure 1:
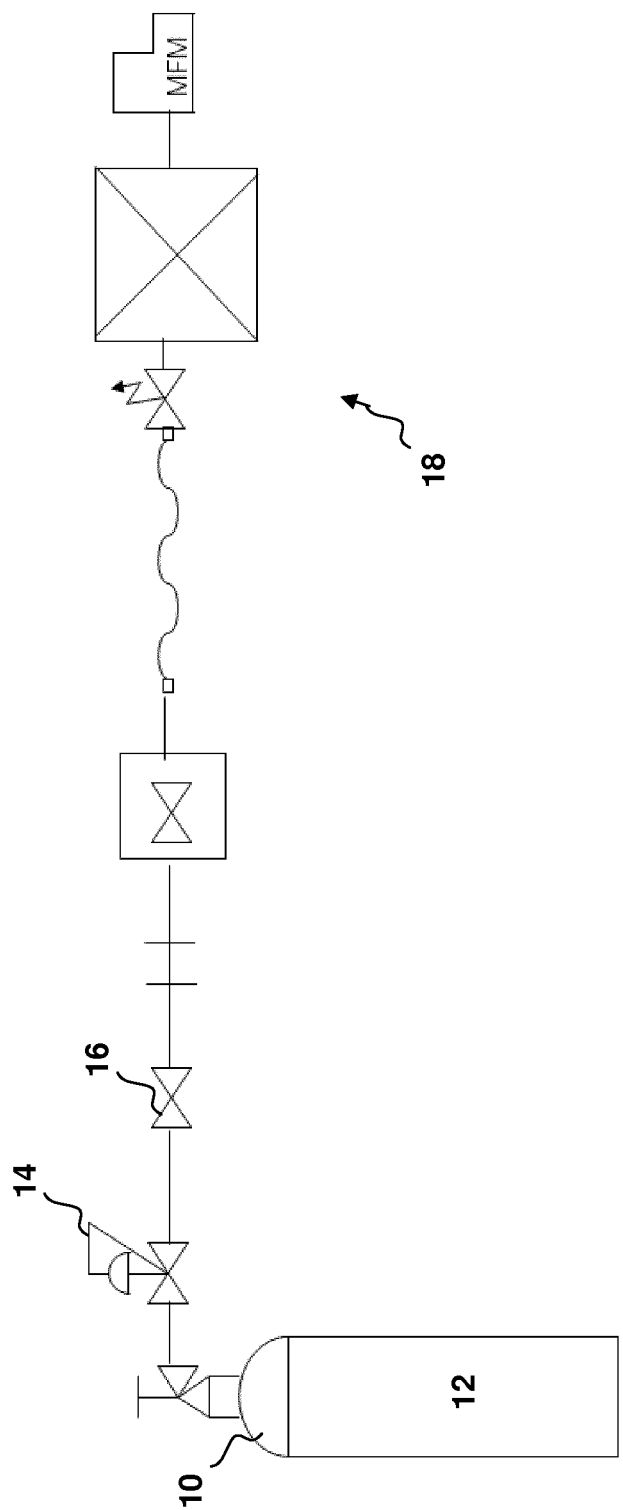
FIG. 1 is a schematic diagram of a gas cylinder assembly attached to a MIG/MAG welding system.
Figure 2:
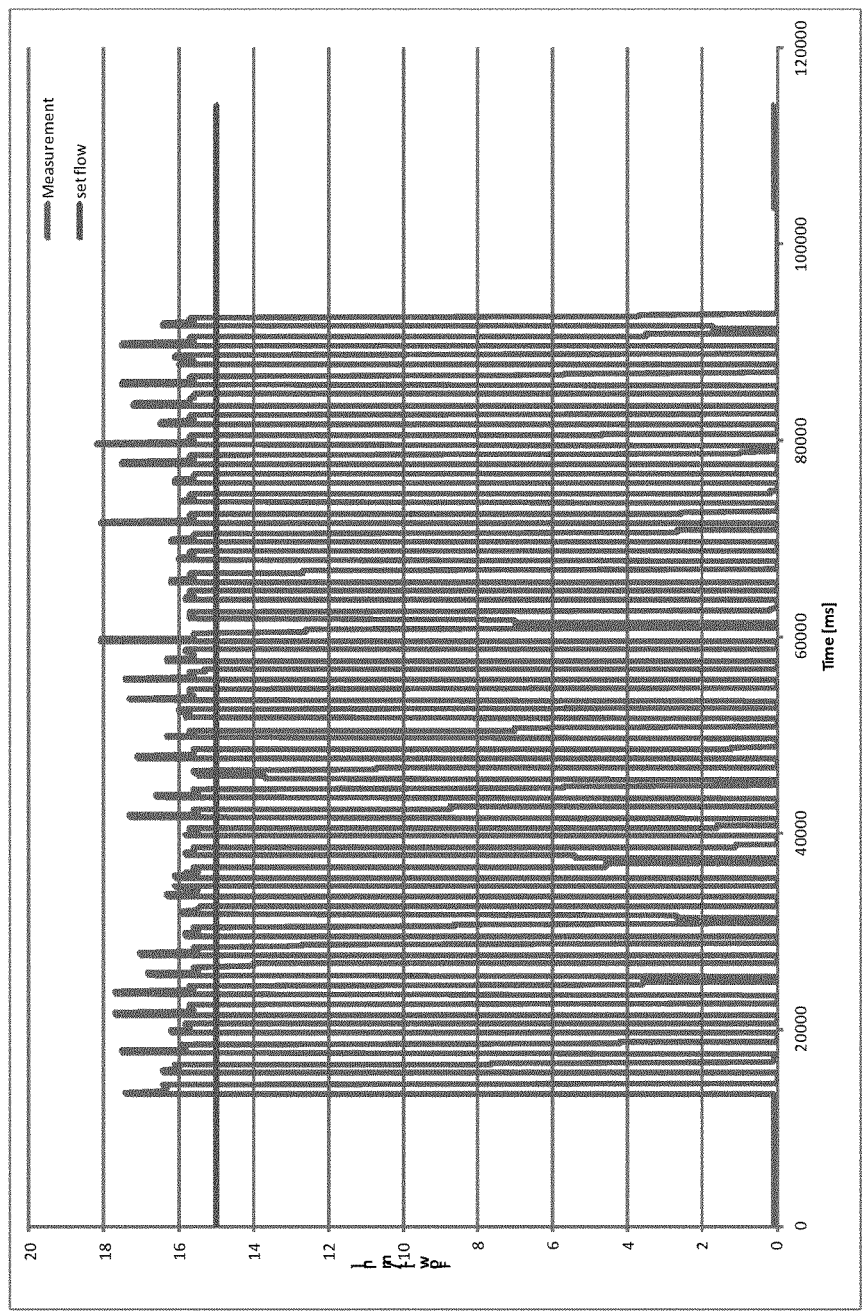
FIG. 2 is a graph showing the problem of surge in a system similar to that of FIG. 1.

The gas cylinder assembly 10 comprises a gas cylinder 12 as described in relation to the example of FIG. 1. The gas cylinder 12 has a body 102 formed from steel, aluminium and/or composite materials and is adapted and arranged to withstand internal pressures up to approximately 900 bar g. An aperture 104 is located at a proximal end of the gas cylinder body 102 opposite to the base and comprises a screw thread (not shown) adapted to receive the valve and regulator assembly 14.

The gas cylinder body 102 and valve and regulator assembly 14 define a pressure vessel (in this embodiment, in the form of the gas cylinder 12) having an internal volume V. The internal volume V is fixed. By this is meant that the structure of the gas cylinder 12 is such that the internal volume V thereof (and, concomitantly, the volume of a gas contained therein) can be assumed not to vary by a significant degree in use, storage or in dependence upon environmental conditions such as temperature, pressure or humidity. The internal volume V of the gas cylinder 12 is intended to include the entire volume within the gas cylinder body 102 and the valve and regulator assembly 14. In other words, the internal volume V is the total internal volume within the gas cylinder assembly 10 where gas is held under pressure.

Any suitable fluid may be contained within the gas cylinder assembly 10. However, the present embodiment relates, but is not exclusively limited to, purified permanent gases which are free from impurities such as dust and/or moisture. Non-exhaustive examples of such gases may be: Oxygen, Nitrogen, Argon, Helium, Hydrogen, Methane, Nitrogen Trifluoride, Carbon Monoxide, Krypton or Neon.

The valve and regulator assembly 14 comprises a housing 106 including an integrated pressure regulator and a fill port to enable filling of a gas cylinder. Non-exhaustive examples of suitable regulators may be single or double diaphragm regulators. However, the skilled person would be readily aware of variations that could be used with the present invention.

The valve and regulator assembly 14 is operable to receive gas from the interior of the gas cylinder 12 at full cylinder pressure (e.g. 100 bar), but to deliver gas at a substantially constant fixed low pressure (e.g. 5 bar) to the outlet. This is achieved by a feedback mechanism whereby a poppet valve, operable to translate towards and away from a valve seat, is connected to a diaphragm. The pressure of gas downstream of the valve is operable to act on the diaphragm in opposition to the biasing force of a spring.

A graspable handle 108 is provided to enable a user to adjust the biasing force of the spring, thereby moving the position of the diaphragm and, as a result, adjusting the equilibrium spacing between the poppet valve and the valve seat. This enables adjustment of the dimensions of the aperture through which the high pressure gas flow from the outlet can pass, and so allows the output pressure to be set.

A through-hole 110 is formed in the housing 108. The through-hole 110 is closed by means of a feed through 112 which enables components (such as wires) to be fed through from externally of the gas cylinder 12 to the interior of the gas cylinder 12. The feed through 112 functions as a high pressure seal maintaining the integrity of the gas cylinder 12.

A guard body 114 is provided. The guard body 114 comprises a clamshell structure connected to the valve and regulator assembly 14. The guard body 114 is arranged to surround the valve and regulator assembly 14 in use. The guard body 114 is substantially elliptical and has a circular cross-section. Provision may be made within the structure of the guard body 114 for one or more access ports. These access ports may include items such as a display (described later), or provide access to the outlet, the fill port or the graspable handle 106 to enable operation and selection of gas dispensation modes or pressures.

The guard body 114 is arranged to surround the valve and regulator assembly 14, and provides both structural and environmental protection for the valve and regulator assembly 14 and related components. In other words, the guard body 114 forms a housing or cover for the valve and regulator assembly 14. Consequently, the guard body 114 together form an enclosure and surround for the valve and regulator assembly 14.

Further, the guard body 114 improves the aesthetic appearance of the cylinder assembly 10 and enables further items to be contained within; for example, an electronic display or additional electronics or components required for operation of the gas cylinder assembly as will be described later.

The guard body 114 may be made from any suitable material. Nevertheless, injection moulded plastics material is the preferred material choice due to the ease of manufacture and the range of design freedom. Plastics materials such as ABS or polycarbonate may be used in non-limiting and non-exhaustive examples.

The gas cylinder assembly 10 is provided with a sensor assembly 200. The sensor assembly 200 is arranged to measure the density of the gas within the internal volume V of the gas cylinder 12. The sensor assembly 200 is shown in greater detail in FIGS. 3 and 4 and, in one part, comprises a gas sensor in the form of a quartz crystal oscillator 202 connected to a drive circuit 204 and a battery 206.

Figure 3:
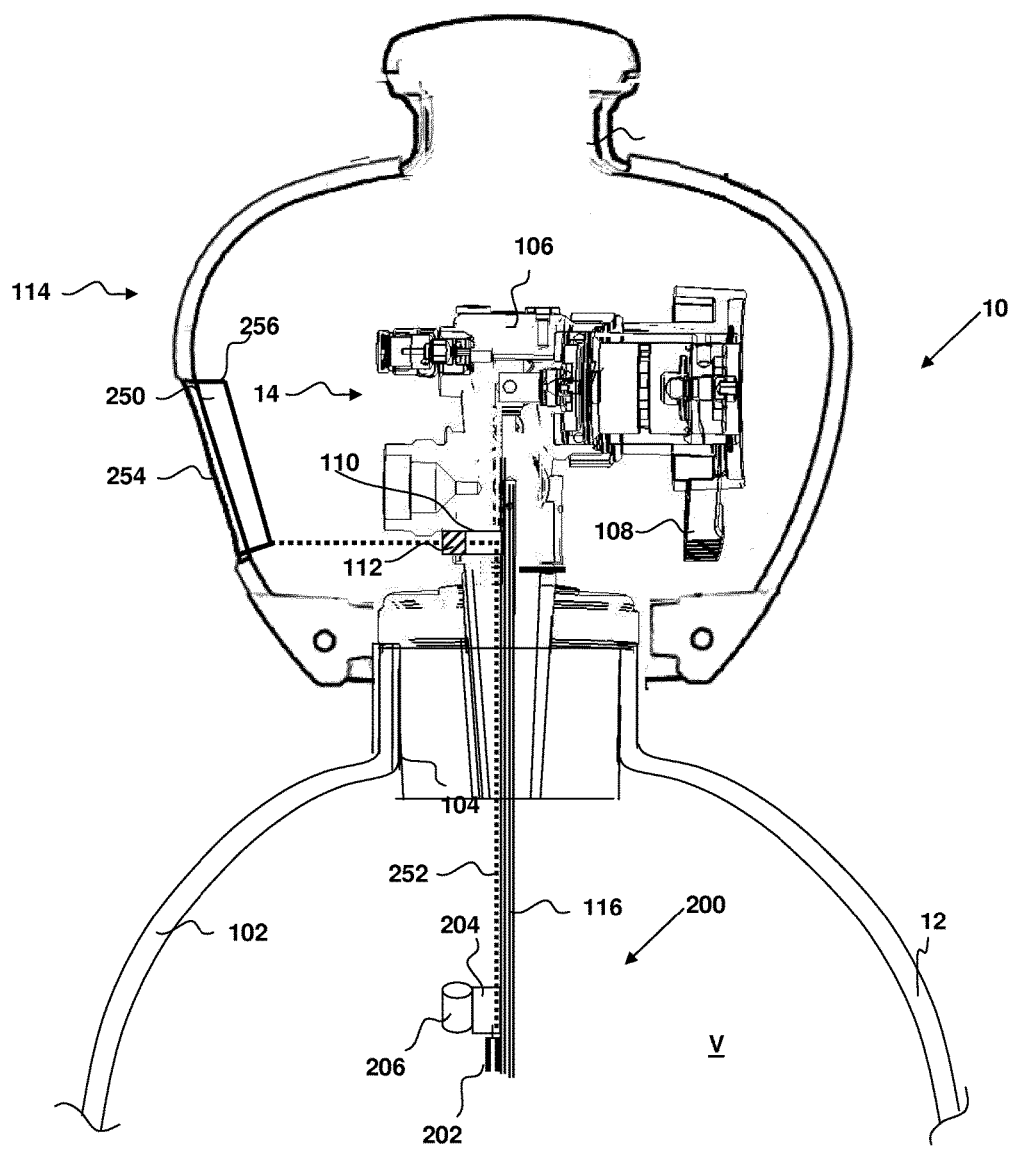
FIG. 3 is a schematic diagram showing an upper part of the gas cylinder assembly and a sensor assembly and data module according to an embodiment of the present invention.

The sensor assembly 200 is, as shown in FIG. 3, located at a distal end of a feed pipe 116 attached to the valve and regulator assembly 14. The feed pipe 116 is arranged to feed gas to/from the interior of the gas cylinder 12 via the valve and regulator assembly 14, and extends from the valve and regulator assembly 14 into the interior of the gas cylinder body 102.

Therefore, the sensor assembly 200 may be physically connected to the valve and regulator assembly 14 for convenience of installation but, in use, the gas sensor elements are located within the interior of the gas cylinder body 102. This provides optimal measurement conditions and reduces the effect of convection and/or thermal interference on the measurements taken by the sensor assembly 200.

In this arrangement, the quartz crystal oscillator 202 is constantly under isostatic pressure within the internal volume V of the gas cylinder 12 and, consequently, does not experience a pressure gradient. In other words, any mechanical stress originating from the pressure difference between the internal volume V of the gas cylinder 12 and the external environment is expressed across the feed through 112.

Further, the location of parts of the sensor assembly 200 entirely within the gas cylinder body 102 provides additional flexibility when configuring gas cylinders 12. In particular, location of relatively fragile electronic components entirely within the strong metal or composite walls of the gas cylinder 12 provides considerable protection from environmental or accidental damage. This is particularly important, for example, in storage areas or depots, where gas cylinders 12 are located adjacent other gas cylinders 12, heavy machinery or rough surfaces.

Furthermore, the location of the electronic components of the sensor assembly 200 within the internal volume V of the gas cylinder 12 enables larger components to be provided which otherwise might not be suitable for use on the external surface of a cylinder 12. For example, a larger battery may be provided in order to increase the operational lifetime of the sensor assembly 200.

Additionally, the internal location of the sensor assembly 200 protects the electronic components from environmental conditions such as salt, water and other contaminants. This would allow, for example, a high impedance circuit which is highly sensitive to salt and water damage to be used as part of the sensor assembly 200.

However, in a variation of the above embodiments, part of the sensor assembly may be located within the internal volume V of the gas cylinder 12 and a part may be located externally thereof. For example, the drive circuit 204 may be located within the gas cylinder 12 whilst the battery 206 may be located outside the gas cylinder 12. This arrangement enables the more fragile components of the sensor assembly to be protected from damage and contaminants, whilst the battery 206 is readily accessible for maintenance and replacement.

The sensor assembly 200 further comprises, and is connected to, a data module 250. The datas module 250 is shown in FIG. 3 and, schematically, in FIG. 4a. The data module 250 is located within the interior of the guard body 114. The data module 250 is connected to the sensor assembly 200 by means of an electrical connection 252 arranged to extend through the feed through 112. However, other connections may be utilised; for example, wireless communication through NFC (near field communication), protocols such as Bluetooth or other wireless methods.

The data module 250 comprises a display screen 254 which, in this embodiment, is integrated into the guard body 114. The display 254 may comprise, for example, an E-ink display to minimise power consumption and maximise visibility of the display. Alternatively, a Liquid Crystal Display (LCD) or Organic Light Emitting Diode (OLED) display may be used.

Figure 4A:
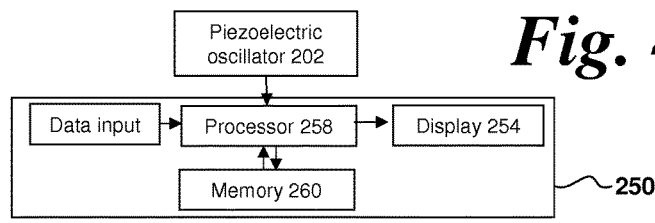
FIG. 4a is a schematic diagram of the data module of FIG. 3.

A housing 256 is also provided which is operable to contain electronic components of the data module including a processor 258 (shown in FIG. 4a), a memory 260 and other electronic components. The processor 258 may receive inputs from the quartz crystal oscillator 202 and drive circuit 204. The processor 258 may comprise and suitable arrangement, such as an Application Specific Integrated Circuit (ASIC) or Field Programmable Gate Array (FPGA). The processor 258 is programmed to calculate, display and communicate parameters useful to users of the cylinder 12 as will be described. As shown in FIG. 4a, the processor 258 is operable to receive an input from the piezoelectric oscillator 202, data input (e.g. from a user via switches or keys) and from the memory 260 which may store look up tables or other data in permanent (e.g. flash memory) or temporary (e.g. RAM) memory storage.

The data module 250 may log various parameters as measured by the piezoelectric oscillator 202 of the sensor assembly 200 as will be described. The data module 250 may also comprise a wireless transmitter and receiver (not shown) to enable remote transmission of data to/from the data module 250 to additional devices, as will be described later.

The piezoelectric oscillator 202 and drive circuit 204 of the sensor assembly 200 will now be described in more detail with reference to FIG. 4b. The quartz crystal oscillator 202 comprises a small, thin section of cut quartz. Quartz demonstrates piezoelectric behaviour, i.e. the application of a voltage across the crystal causes the crystal to change shape, generating a mechanical force. Conversely, a mechanical force applied to the crystal produces an electrical charge.

Two parallel surfaces of the quartz crystal oscillator 202 are metallised in order to provide electrical connections across the bulk crystal. When a voltage is applied across the crystal by means of the metal contacts, the crystal changes shape. By application of an alternating voltage to the crystal, the crystal can be caused to oscillate.

The physical size and thickness of the quartz crystal determines the characteristic or resonant frequency of the quartz crystal. Indeed, the characteristic or resonant frequency of the crystal 202 is inversely proportional to the physical thickness between the two metallised surfaces. Quartz crystal oscillators are well known in the art and so the structure of the quartz crystal oscillator 202 will not be described further here.

The resonant vibration frequency of a quartz crystal will vary depending upon the environment in which the crystal is located. In a vacuum, the crystal will have a particular frequency. However, this frequency will change in different environments. For example, in a fluid, the vibration of the crystal will be damped by the surrounding molecules of the fluid and this will affect the resonant frequency and the energy required to oscillate the crystal at a given amplitude.

The quartz crystal oscillator 202 of the present embodiment is tuning fork-shaped and comprises a pair of tines 202a (FIG. 4b) approximately 5 mm long arranged to oscillate at a resonant frequency of 32.768 kHz. The tines 202a of the fork oscillate normally in their fundamental mode, in which they move synchronously towards and away from each other at the resonant frequency.

Such crystals are commonly available at relative low cost. In contrast to the majority of quartz crystal oscillators which are used in vacuo, in the present embodiment the quartz crystal oscillator 202 is exposed to the gas under pressure in the internal volume V of the gas cylinder 12.

Figure 4B:
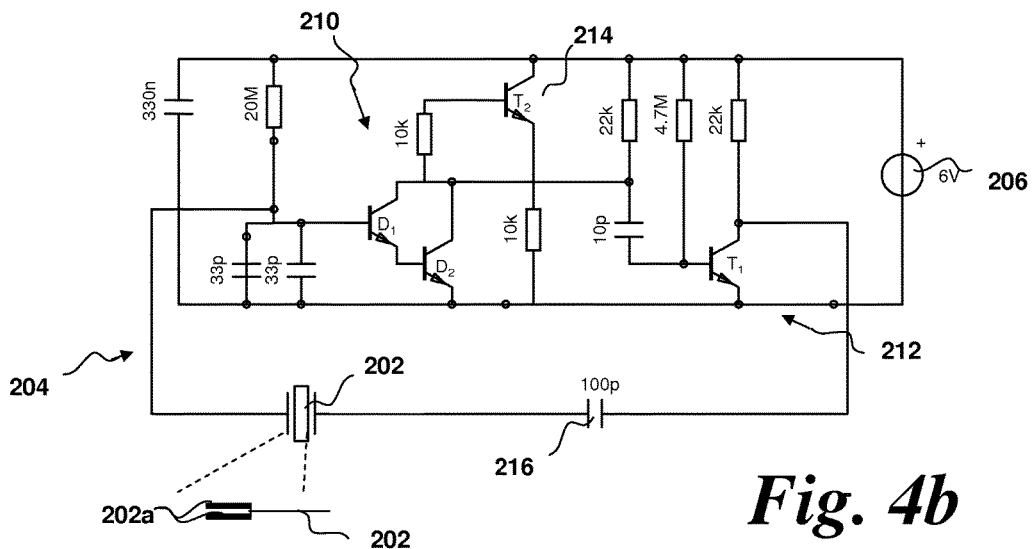
FIG. 4b is a schematic diagram of a drive circuit for use with the sensor assembly of FIG. 3.
Figure 5:
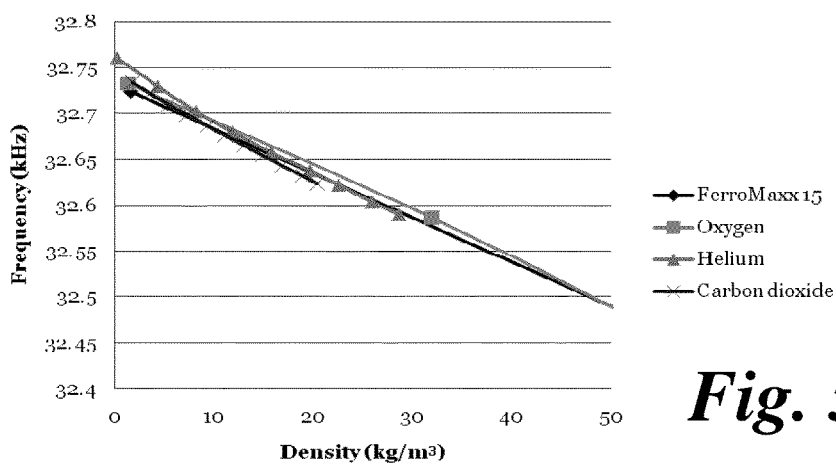
FIG. 5 shows a graph of quartz crystal frequency (kHz) on the Y-axis as a function of density ($kg/m^3$) for a number of different gases.

An example of a drive circuit 204 for driving the quartz crystal oscillator 202 is shown in FIG. 4b. The drive circuit 204 must meet a number of specific criteria. Firstly, the quartz crystal oscillator 202 of the present invention may be exposed to a range of gas pressures; potentially, the pressures may vary from atmospheric pressure (when the gas cylinder 12 is empty) to around 900 barg if the gas cylinder contains a pressurised gas such as hydrogen. Thus, the quartz crystal 202 is required to operate (and restart after a period of non-use) under a wide range of pressures.

As the pressure in the gas cylinder 12 increases, the oscillation of the quartz crystal oscillator 202 will become increasingly damped, and will require a higher gain to be provided by an amplifier in the drive circuit 204. However, if too high an amplification is provided, the drive circuit 204, the response from the quartz crystal oscillator 202 may become difficult to distinguish. In this case, the drive circuit 204 may simply oscillate at an unrelated frequency, or at the frequency of a non-fundamental mode of the quartz crystal oscillator 202. As a further limitation, the drive circuit 204 must be low power in order to run on small low power batteries for a long time with or without supplementary power such as photovoltaic cells.

In order to drive the quartz crystal oscillator 202, the drive circuit 204 essentially takes a voltage signal from the quartz crystal oscillator 202, amplifies it, and feeds that signal it back to the quartz crystal oscillator 202. The fundamental resonant frequency of the quartz crystal oscillator 202 is, in essence, a function of the rate of expansion and contraction of the quartz. This is determined in general by the cut and size of the crystal.

However, external factors also affect the resonant frequency. When the energy of the generated output frequencies matches the losses in the circuit, an oscillation can be sustained. The drive circuit 204 is arranged to detect and maintain this oscillation frequency. The frequency can then be measured by the processor 258, used to calculate the appropriate property of the gas required by the user and, if required, output to a suitable display means (as will be described later).

When used with the quartz crystal oscillator 202, the processor 258 may be configured to measure the frequency f or period of the signal from the drive circuit 204. This may be achieved by, for example, counting oscillations over a fixed time, and convert that frequency into a density value using an algorithm or look-up table. This value is passed to the processor 258 which is configured to perform, based on the supplied inputs, a calculation to determine the mass of the gas and additional parameters for the gas in the gas cylinder 12.

The theory and operation of the sensor assembly 200 will now be described with reference to FIGS. 5 to 10.

The quartz crystal oscillator 202 has a resonant frequency which is dependent upon the density of the fluid in which it is located. Exposing an oscillating tuning fork-type crystal oscillator to a gas leads to a shift and damping of the resonant frequency of the crystal (when compared to the resonant frequency of the crystal in a vacuum). There are a number of reasons for this. Whilst there is a damping effect of the gas on the oscillations of the crystal, the gas adheres to the vibrating tines of the tuning fork crystal oscillator 202 which increases the mass of the oscillator. This leads to a reduction in the resonant frequency of the quartz crystal oscillator according to the motion of a one-sided, fixed elastic beam:

$$\frac{\Delta\omega}{\omega_0} = \frac{\rho t}{2\rho_q w}\left(c_1 + c_2 \frac{\partial}{t}\right) \quad 1)$$

Where $$\frac{\Delta\omega}{\omega_0}$$

is the relative change in resonant angular frequency, $\rho$ is the gas density, t is the thickness of the quartz oscillator, $\rho_q$ is the density of the quartz oscillator and w is the width of the fork. $c_1$ and $c_2$ are geometrically dependent constants and $\partial$ is the thickness of the surface layer of gas as defined by:

$$\partial = \sqrt{\frac{2\eta}{\rho\omega_0}} \quad 2)$$

Where $\eta$ is the temperature dependent viscosity of the gas.

The two parts of equation 1) relate to a) the additive mass of the gas on the tines of the quartz crystal oscillator 202 and to b) the shear forces arising on the outermost surface layer of the tines during oscillation. The equation can thus be rewritten in terms of frequency and simplified to:

$$\Delta f = A\rho + B\sqrt{\rho} + C \quad 3)$$

Where $$A = \frac{c_1 t}{2\rho_q w} f_0, \quad B = \frac{c_2}{2\rho_q w}\sqrt{\frac{\eta}{\pi}}\sqrt{f_0}$$

and C is an offset constant and $f_0$ is the natural resonant frequency of the crystal in a vacuum.

It has been found by the inventors that a suitably good approximation can be obtained by approximating:

$$\Delta f \approx \Delta\rho \quad 4)$$

Figure 6:
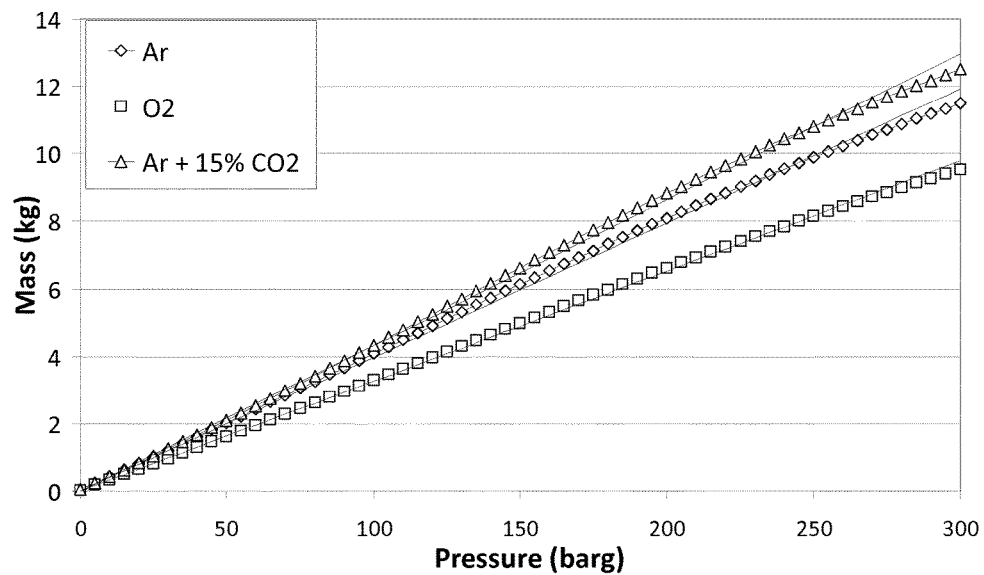
FIG. 6 shows a graph of gas mass (in kg) on the Y-axis as a function of pressure (bar g) on the X-axis for Argon, Oxygen and an Argon:Carbon Dioxide mixture.

Consequently, to a good approximation, the change in frequency is proportional to the change in density of the gas to which the quartz crystal oscillator is exposed. FIG. 6 shows, for a number of different gases/gas mixtures, that the resonant frequency of the quartz crystal oscillator 202 varies linearly as a function of density.

The quartz crystal oscillator 202 is particularly suitable for use as a density sensor for commercially-supplied gases. Whilst, as set out above, the change in frequency is approximately equal to the change in density, it is relatively straightforward to implement a more thorough relationship in practice. Therefore, in a physical measurement arrangement, the following equation (based on equation 3)) is used:

$$\rho_t = a\left(\frac{f_t}{1000}\right)^2 + b\frac{f_t}{1000} + c \quad 5)$$

In equation 5), $\rho_t$ is the density, and $f_t$ is the frequency of oscillation, both measured at time t. a, b and c are constants that are functionally reprogrammable.

As previously described, the internal volume V of gas within the gas cylinder 12 is fixed. Therefore, once the density p of the gas within the internal volume V of the gas cylinder 12 has been obtained from measurement by the sensor assembly 200, the mass M of the gas in the cylinder can be obtained from the following equation:

$$M = \rho V \quad 6)$$

The direct measurement of the density $\rho$ of the gas, therefore, enables the calculation of the mass of gas remaining in the gas cylinder 12. In practice, in a real system knowing the volume of the cylinder, the mass of gas remaining can be calculated in a straightforward manner from a multiplication of the resonant frequency by a known factor.

Measurement of the mass of gas in this way has a number of advantages over known arrangements. For example, the mass measured according to an embodiment of the invention is corrected intrinsically for temperature.

Further, the mass of gas measured according to an embodiment of the present invention is intrinsically corrected for compressibility Z. In a conventional arrangement, for example, utilising a Bourdon gauge in order to obtain gas contents from pressure, the compressibility of the gas needs to be corrected for. This is particularly important at high pressures, where the compressibility Z is not proportional to the gas pressure in the way expected of an ideal gas.

The automatic compensation for compressibility is illustrated with reference to FIGS. 6 and 7. FIG. 6 shows a graph of gas mass (in kg) on the Y-axis as a function of Pressure (bar g) for Argon, Oxygen and an Argon:Carbon Dioxide mixture. As shown in FIG. 6, the masses of the different gases vary with increasing pressure. Further, at high pressures in excess of 250 bar g, there is no longer a linear relationship between mass and pressure.

Figure 7:
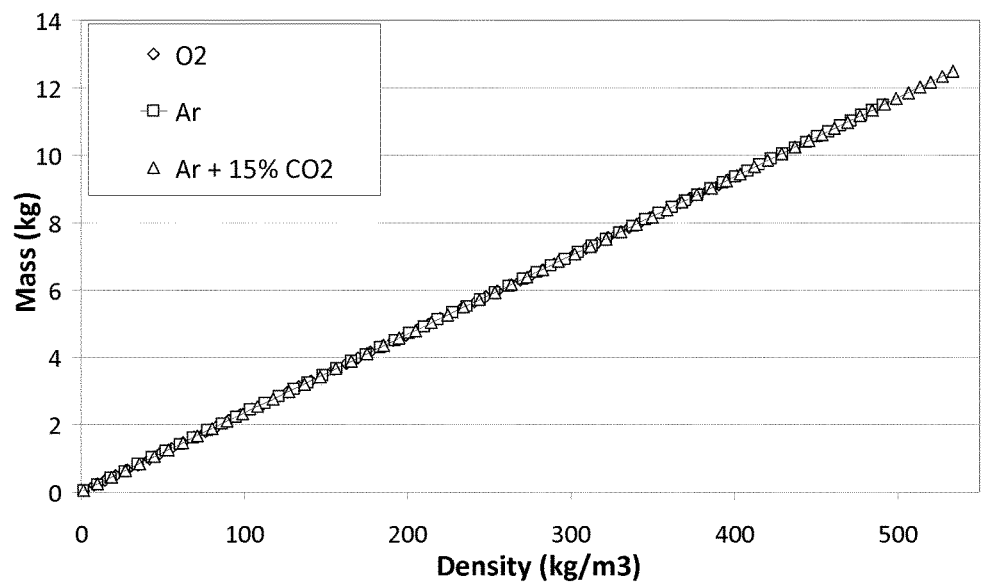
FIG. 7 shows a graph of gas mass (in kg) on the Y-axis as a function of density (in $kg/m^3$) on the X-axis for the same three gases (Argon, Oxygen and an Argon:Carbon Dioxide mixture) as shown in FIG. 6.

FIG. 7 shows a graph of gas mass (in kg) on the Y-axis as a function of Density (in kg/m$^3$) for the same three gases (Argon, Oxygen and an Argon:Carbon Dioxide mixture) as FIG. 6. In contrast to FIG. 6, it can be seen that the mass of gas as a function of density is identical for each gas/gas mixture. Further, the relationship is still linear at high densities. Consequently, the quartz crystal oscillator 202 can be both high resolution and highly linear with density.

As outlined above, the arrangement of the present invention enables mass measurement to very high accuracy with a resolution of parts per million. Coupled with the linear response of the quartz density sensor 202 at high densities and pressures (as illustrated in FIGS. 6 and 7), the high accuracy enables very light gases such as H$_2$ and He to be measured accurately.

It is also useful to know the contents of the gas cylinder remaining in terms of a percentage. This may be done in accordance with the equation below:

$$\text{Contents } (\%) = \frac{\rho}{\rho_f} \times 100 \quad\quad 7)$$

Where $\rho$ is the measured density and $\rho_f$ is the density when the cylinder is full. In practice, $\rho_f$ may be measured directly. Alternatively, given a known gas and known conditions (e.g. 300 barg at 15° C.), the value of $\rho_f$ can be assumed to take a constant value and this may, for example, be stored in a look up table in the processor 258.

In addition to measurement of the static pressure within a gas cylinder 12, the sensor assembly 200 is capable of measuring mass flow rate into or from the gas cylinder 12.

Gas density at atmospheric pressure is only on the order of 1 g/liter, and normal gas usage rates are often just a few liters per minute. The inventors have found that the quartz crystal oscillator 202 is sufficiently stable and accurate to enable mass flow of gas exiting the gas cylinder 12 in to be measured by means of the changing density indicated. The mass flow rate $$\frac{\partial M}{\partial t}$$

is calculated from equation 8):

$$\frac{\partial M}{\partial t} = V \frac{\Delta \rho}{\Delta t} \quad\quad 8)$$

where V is the volume, $\Delta \rho$ the change in density indicated over time interval $\Delta t$. In this instance, the operation of the sensor assembly 200 requires the drive circuit 204 to integrate over a number of oscillation cycles of the quartz crystal oscillator 202.

Figure 8:
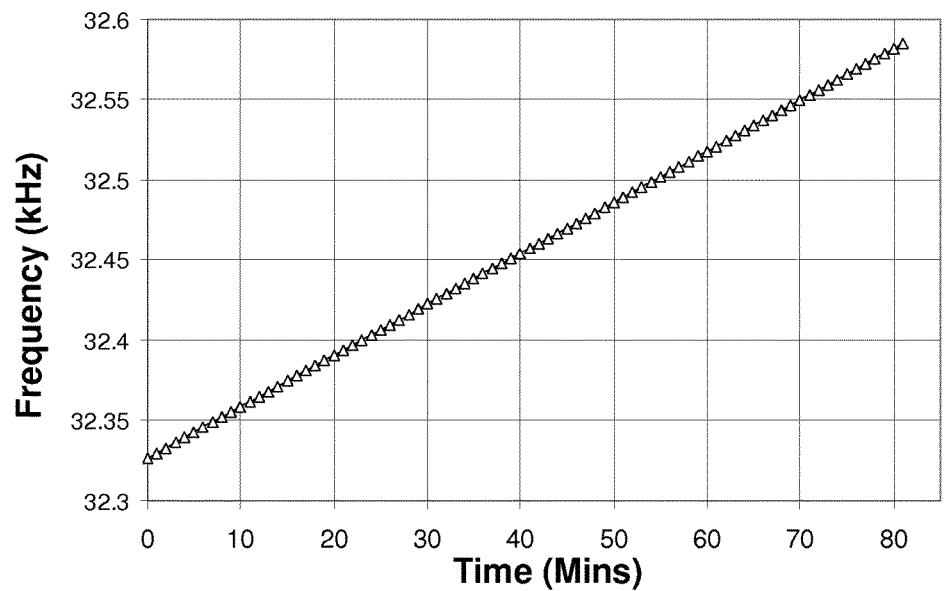
FIG. 8 shows a graph of frequency (in kHz) on the Y-axis as a function of time (in minutes) on the X-axis for a flow rate of 12 l/min from a 50 liter gas cylinder at a pressure of 100 bar g.
Figure 9:
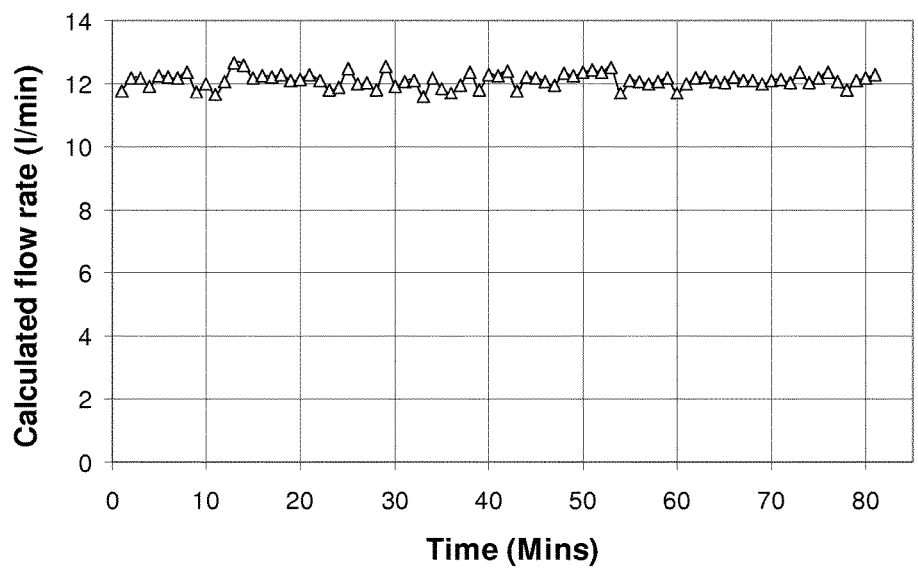
FIG. 9 shows a graph of the calculated flow rate (in liters per minute) on the Y-axis as a function of time (in minutes) on the X-axis for the 50 liter cylinder at a pressure of 100 bar g.

FIGS. 8 and 9 illustrate experimental data of mass flow detection. FIG. 8 shows a graph of frequency (in kHz) on the Y-axis as a function of time (in minutes) on the X-axis for a 12 liter per minute flow rate from a 50 liter cylinder at ~100 bar pressure indicated. FIG. 9 shows a graph of the calculated flow rate (in liters per minute) on the Y-axis as a function of time (in minutes) on the X-axis for the 50 liter cylinder at ~100 bar pressure.

These figures illustrate that the mass flow rate of gas from a gas cylinder 12 can be determined from a measurement of change of density with time. Consequently, the mass flow rate can be calculated with sufficient accuracy and time resolution using the quartz crystal oscillator 202 and drive circuit 204.

Figure 10:
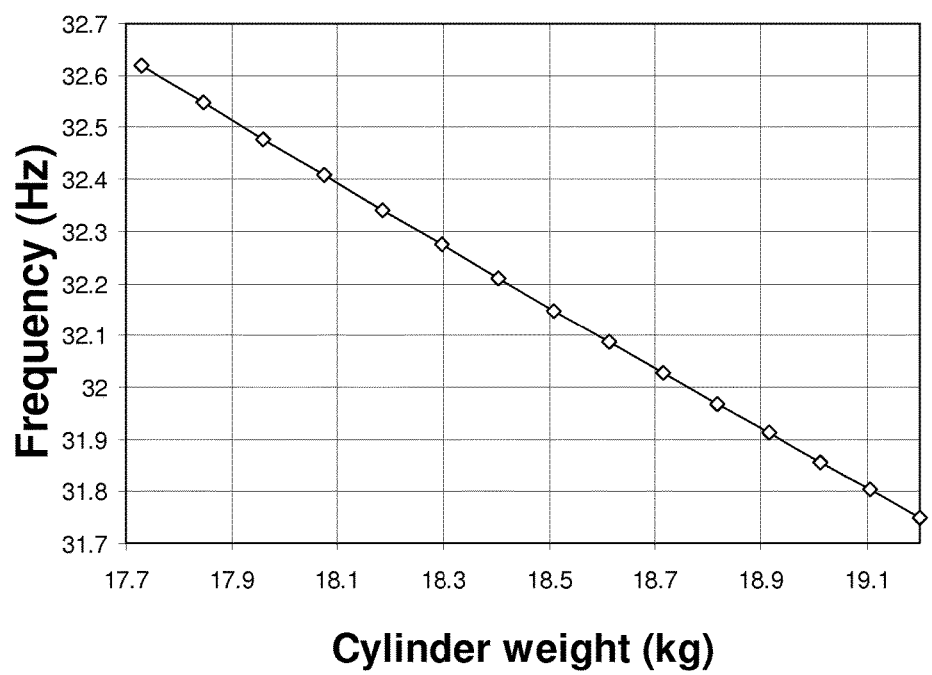
FIG. 10 shows a graph of frequency (in kHz) on the Y-axis as a function of gas cylinder mass (in kg) on the X-axis for a typical gas cylinder.
Figure 11:
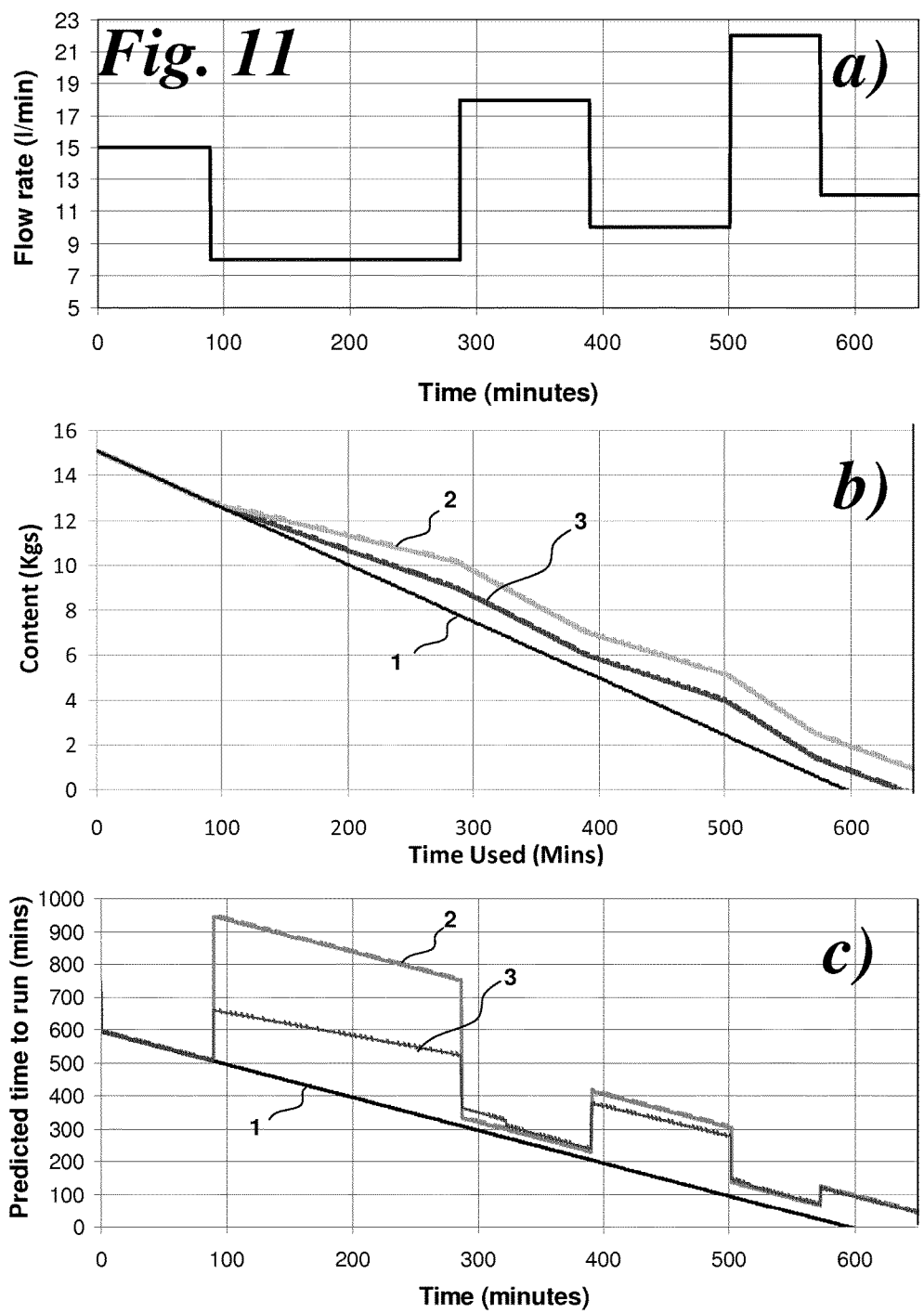
FIG. 11a shows a graph of example data illustrating flow rate in liters per minute as a function of time in minutes using an initial flow rate of 15 liters/minute.
FIG. 11b shows a graph of cylinder contents as a function of time in minutes based on the example flow rates shown in FIG. 11a for a straight-line prediction, an actual measurement and a predicted measurement using a method according to the present invention.
FIG. 11c shows a graph of predicted time to run (in minutes) from a gas cylinder as a function of time in minutes based on the example flow rates shown in FIG. 11a for a straight-line prediction, instantaneous flow rate measurement and a predicted measurement using a method according to the present invention.

FIG. 10 illustrates further experimental data and illustrates a graph of frequency (in kHz) on the Y-axis as a function of total cylinder mass (in kg) on the X-axis. As can be seen, the graph is, to a high degree of accuracy, approximately linear. Therefore, FIG. 11 shows that the mass of gas within the gas cylinder 12 can be measured accurately with the quartz crystal oscillator 202.

Importantly, the data obtained from the sensor assembly 200 may be used to present data on the run out time, i.e. the time before the gas in the cylinder 12 is used up. This is particularly critical in applications such as a hospital oxygen cylinder used in patient transit between hospitals.

A known arrangement is to calculate the run out time based on a given, set flow rate. However, such a run out time is in general inaccurate for reasons set out above. Such an approach cannot take into account varying flow rates, gas surges and other phenomena. It may underread, or overread by unknown amounts.

Further, a known method for carrying out the measurement of such a time (T$_{run}$) can be calculated from knowledge of the flow rate (discussed above), mass contents of the cylinder 12 and the current time (T$_c$) via the following equation:

$$T_{run} = T_c + \frac{M}{\frac{\partial M}{\partial t}} \quad\quad 9)$$

This is known as run out time calculated from the instantaneous flow rate, i.e. an extrapolation of the flow rate as currently measured. This approach provides more accurate measurement which can be adjusted as the flow rate changes. However, such an approach is likely to be inaccurate because it is only able to take account of the current situation in flow rate. As discussed above, the use of equation 9) will generally over-estimate the amount of gas remaining in the gas cylinder because it will be unable to factor in past use patterns which may include surge behaviour. For some applications, for example, healthcare applications, this over-reading may be a critical issue.

The present invention relates to a method in which the time to run of a gas cylinder can be estimated from, amongst other things, the actual consumption rate. Further, the time remaining, time used, average flow rate and stored flow rates can be used as a quality check to verify the method.

The method of the present invention is based on equation 10) below:

$$T_{run} = \frac{M}{F_{AVG}} \quad\quad 10)$$

Where M is the mass of gas remaining in the gas cylinder 12, measured in kilograms (kg) and F$_{AVG}$ is the average flow rate (in kg/min) which is determined as set out below.

The average flow rate F$_{AVG}$ is determined based on equation 11) below:

$$F_{AVG} = DE + (1-E)\frac{\sum_{i=0}^{n} F_i}{n} \quad\quad 11)$$

Where D is a base flow rate, E is a variable scaling factor (as will be described later), and $F_i$ is a measurement of flow rate, where the second function is a sum of n flow rate measurements, i being in the range of 0 to n.

Consequently, equation 11) comprises two functions. One is a function of a base flow rate and the other is a function of the average measured flow rate. The scaling factor E is predetermined and as E varies, the proportion of the first and second functions comprising equation 11) varies.

The inventors have found, for the first time, that the behaviour of gas flow from a gas cylinder is dependent upon the contents of the gas cylinder. Therefore, the scaling factor E is introduced to enable a transition between the different regimes of a gas cylinder, depending upon whether it is full, empty or partially full. The parameter E is selected from a look up table as set out below in Table 1:

TABLE 1

| Content (%) | E |
| --- | --- |
| 100 to 90 | 0.8 |
| 90 to 60 | 0.5 |
| 60 to 30 | 0.2 |
| Less than 30 | 0.1 |

Therefore, as shown in Table 1, as the contents of the gas cylinder decrease, the value of E concomitantly decreases. This causes the first function of equation 11) to decrease in weight relative to the second function as the gas cylinder 12 empties.

As a result, at high fill levels of the gas cylinder, the flow rate is approximately the base flow rate, D, modified to two parts in ten by the average flow rate. This may be set at any desired value; for example, 15 liters/minute. In kg/min, this corresponds to a value of D of approximately 0.03.

At low cylinder fill levels, $F_{AVG}$ is dominated by the average of the previous n measurements of the flow rate.

The inventors have found that this equation models the behaviour of a gas cylinder well. That is because, at high cylinder fill levels, a base flow rate can be more readily achieved. At low fill levels, the delivery is more erratic and so the measurement of the flow rate needs to dominate. In other words, when the cylinder is full it is typical to use a generally fixed flow rate but as the cylinder empties, the inventors have found that it is necessary to predict the flow more accurately.

For many applications, D may be assumed to be a constant. For example, if the valve and regulator assembly 14 is arranged to deliver a fixed flow rate to end applications (for example, 15 liters/minute) then the value of D may be fixed in a memory of the processor 258 and used as a constant.

Alternatively, D may be selected depending upon the starting flow rate if the regulator and/or user is operable to select different flow rates. The flow rate could be entered or selected by a user upon initialisation of a cylinder 12. Alternatively, a value of D could be selected from a plurality of values of D stored in a look up table.

As a further alternative, the value of D could be cross-checked with the measured flow rate and modified if necessary. Whilst the average flow rates calculated as part of the second function of equation 11) are arranged to be updated on a constant (or effectively constant) basis with each measurement, the value for D could be checked for periodically to determine whether there is a discrepancy between the starting value and the actual value. For example, the flow rate could be checked every ten measurements and compared to the stored value of D, with D being updated if necessary. Alternatively, it could be updated every five to fifteen measurements.

It is important to note that the second function of equation 11) is operable to take account of localised variations in flow rate to more accurately predict the remaining time to run. However, D is a more global parameter based on the set flow rate and so needs to be updated less frequently, if at all.

Figure 12:
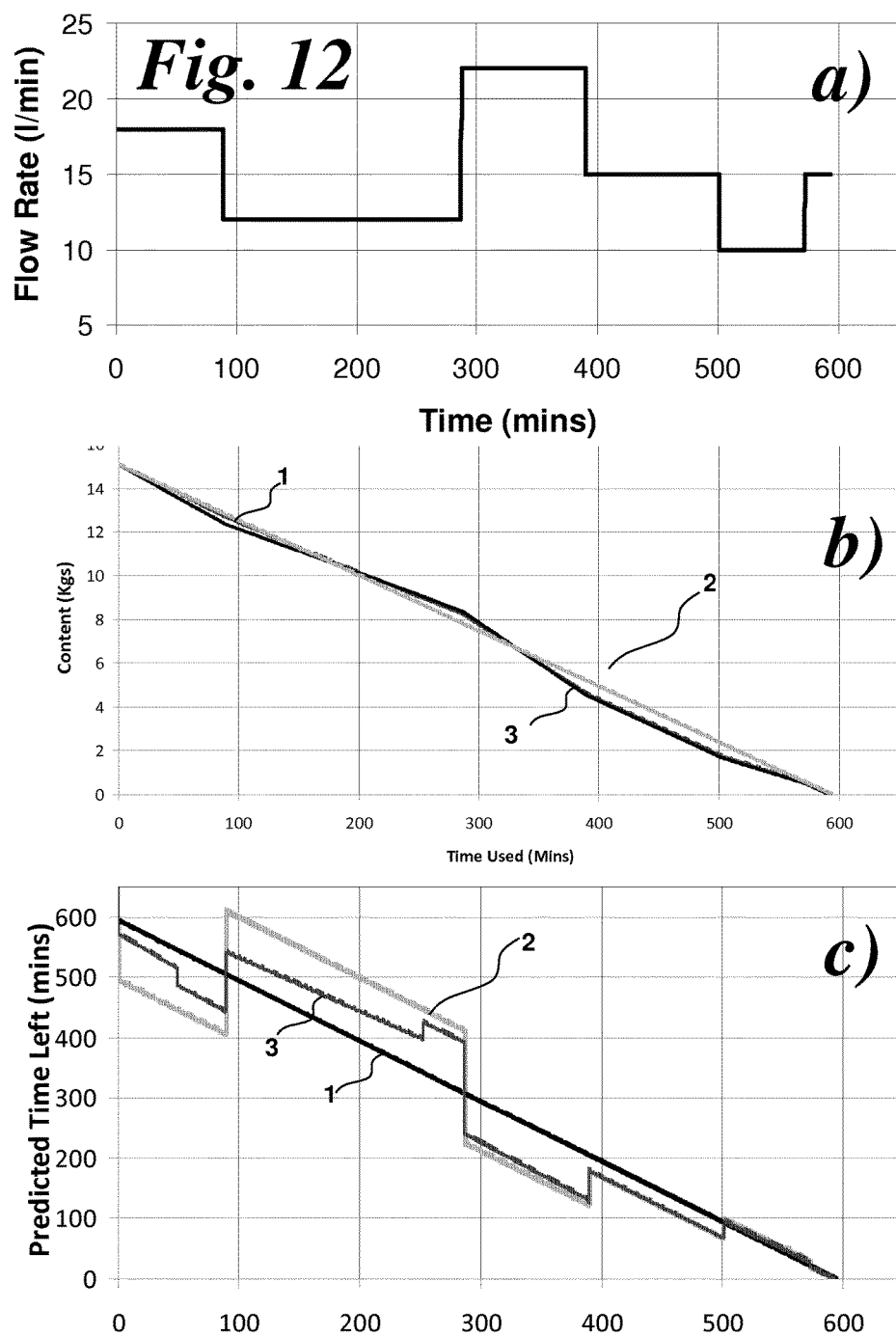
FIG. 12a shows a graph of example data illustrating flow rate in liters per minute as a function of time in minutes using an initial flow rate of 18 liters/minute.
FIG. 12b shows a graph of cylinder contents as a function of time in minutes based on the example flow rates shown in FIG. 12a for a straight-line prediction, an actual measurement and a predicted measurement using a method according to the present invention.
FIG. 12c shows a graph of predicted time to run (in minutes) from a gas cylinder as a function of time in minutes based on the example flow rates shown in FIG. 12a for a straight-line prediction, instantaneous flow rate measurement and a predicted measurement using a method according to the present invention.

FIGS. 11 and 12 illustrate two theoretical examples of the effectiveness of this approach. FIG. 11 shows theoretical data for an initial flow rate of 15 l/min. FIG. 11a) shows the flow rate as a function of time. Note that the flow rate is varied at periodic intervals. FIG. 11b) shows the gas contents of the gas cylinder as a function of time. Line 1 is a linear fit based on the initial flow rate of 15 l/min. Line 2 is an instantaneous flow rate measurement plot in accordance with equation 9). Line 3 is a plot of the method according to the present invention as set out in equations 10) and 11).

FIG. 11c) shows the same three plots as for FIG. 11b) but showing the predicted time to run for each approach. As shown, the linear plot is inaccurate if the flow is varied. The instantaneous flow rate measurement (line 2) hugely over-reads at high cylinder pressures and low flow rates. The method of the present invention (line 3) is more accurate.

FIGS. 12a) to c) show similar data but for a starting flow rate of 18 l/min.

Figure 13:
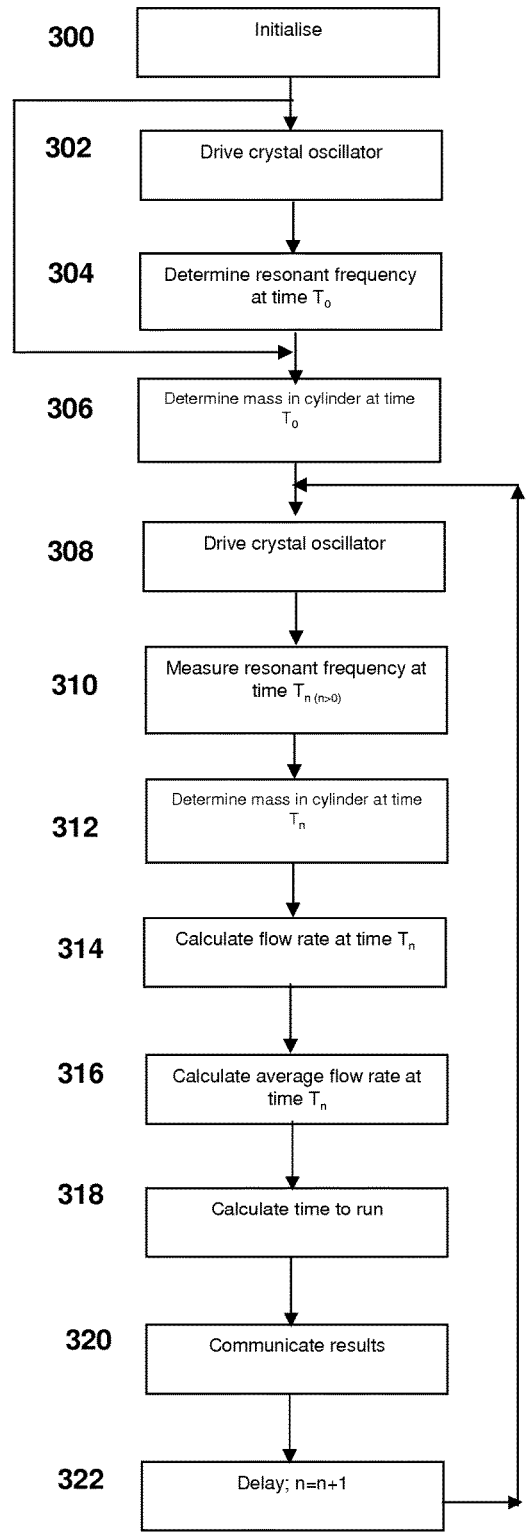
FIG. 13 is a flow chart illustrating a method according to a described embodiment.

A method according to an embodiment of the present invention will now be described with reference to FIG. 13.

Step 300: Initialise Measurement

At step 300, the measurement process in the gas cylinder 12 is initialised. At this stage, at time T0, the gas cylinder is full, i.e. 100% filled.

Alternatively, the measurement may be activated by, for example, a user pressing a button on the outside of the gas cylinder 12. As a further alternative, the measurement may be initiated by means of a remote connection, for example, a signal transmitted across a wireless network and received by the data module 250 wirelessly.

As a further alternative or addition, the data module 250 and sensor assembly 200 may be configured to initialise remotely or on a timer. The method proceeds to step 302.

Step 302: Drive the Quartz Crystal Oscillator

Once initialised, the drive circuit 204 is used to drive the quartz crystal oscillator 202. During initialisation, the drive circuit 204 applies a random noise AC voltage across the crystal 202. At least a portion of that random voltage will be at a suitable frequency to cause the crystal 202 to oscillate. The crystal 202 will then begin to oscillate in synchrony with that signal.

By means of the piezoelectric effect, the motion of the quartz crystal oscillator 202 will then generate a voltage in the resonant frequency band of the quartz crystal oscillator 202. The drive circuit 204 then amplifies the signal generated by the quartz crystal oscillator 202, such that the signals generated in the frequency band of the quartz crystal resonator 202 dominate the output of the drive circuit 204. The narrow resonance band of the quartz crystal filters out all the unwanted frequencies and the drive circuit 204 then drives the quartz crystal oscillator 202 at the fundamental resonant frequency f. Once the quartz crystal oscillator 202 has stabilised at a particular resonant frequency, the method proceeds to step 304.

Step 304: Measure Resonant Frequency of Quartz Crystal Oscillator

The resonant frequency f is dependent upon the conditions within the internal volume V of the gas cylinder. In the present embodiment, the change in resonant frequency $\Delta f$ is proportional in magnitude to the change in density of gas within the gas cylinder 12 and will decrease with increasing density.

In order to make a measurement, the frequency of the quartz crystal oscillator 202 is measured for a period of approximately 1 s. This is to enable the reading to stabilise and for sufficient oscillations to be counted in order to determine an accurate measurement. The measurement of frequency is carried out in the processor 258. The processor 258 may also log the time, $T_0$, when the measurement was started.

Once the frequency has been measured, the method proceeds to step 306.

Step 306: Determine Mass of Gas in Gas Cylinder

Once the frequency of the quartz crystal oscillator 202 has been measured satisfactorily in step 304, the processor 258 then calculates the mass of gas in the gas cylinder 12.

This is done where the mass of the gas can be calculated directly from the density determined in step 304 and the known internal volume V of the gas cylinder 12. This is logged as the 100% fill level of the gas cylinder as measured at time $T_0$.

In the alternative, if the gas is known and is filled to a known condition (e.g. 300 barg at 15 degrees Centigrade), then it is unnecessary to perform steps 302 and 304 and the value at $T_0$ could simply be stored in a look up table.

Either way, the mass could be simply recorded in an internal memory associated with the processor 258 of the sensor assembly 200 for later retrieval. As a yet further alternative, the mass of gas at time $T_0$ could be stored in a memory local to said processor 258. The method then proceeds to step 308.

Step 308: Drive Oscillator

Upon expiry of a time period, for example, 5 minutes, the drive circuit 204 is again used to drive the quartz crystal oscillator 202 as set out in step 304. As described above, the narrow resonance band of the quartz crystal filters out all the unwanted frequencies and the drive circuit 204 then drives the quartz crystal oscillator 202 at the fundamental resonant frequency f. Once the quartz crystal oscillator 202 has stabilised at a particular resonant frequency, the method proceeds to step 310.

Step 310: Measure Resonant Frequency of Quartz Crystal Oscillator

The resonant frequency f is dependent upon the conditions within the internal volume V of the gas cylinder. In the present embodiment, the change in resonant frequency $\Delta f$ is proportional in magnitude to the change in density of gas within the gas cylinder 12 and will decrease with increasing density.

In order to make a measurement, the frequency of the quartz crystal oscillator 202 is measured for a period of approximately 1 s. This is to enable the reading to stabilise and for sufficient oscillations to be counted in order to determine an accurate measurement. The measurement of frequency is carried out in the processor 258. The processor 258 may also log the time, $T_m$ (where m>0) when the measurement occurs. Once the frequency has been measured, the method proceeds to step 312.

Step 312: Determine Mass of Gas in Gas Cylinder

Once the frequency of the quartz crystal oscillator 202 has been measured satisfactorily in step 310, the processor 258 then calculates the mass of gas in the gas cylinder 12 at time $T_m$.

The mass could be simply recorded in an internal memory associated with the processor 258 of the sensor assembly 200 for later retrieval. As a yet further alternative, the mass of gas at time $T_m$ could be stored in a memory local to said processor 258. The method then proceeds to step 314.

Step 314: Calculate Flow Rate

At step 314 the flow rate is calculated. This can be done from the difference between the resonant frequency measured at time $T_m$ and that measured at time $T_{m-1}$. The difference is then divided by the time between $T_m$ and $T_{m-1}$. The frequency change as a function of time is, as described above, proportional to the change in mass of gas, i.e. the flow rate.

Step 316: Calculate Average Flow Rate

The average flow rate can then be calculated based on equation 11) utilising flow rate measurements made in step 314 for the previous n flow rates measured, where n>1 and preferably n=10.

If m<n, then the average flow rate can be determined from the initial base flow rate, D, or another flow rate as specified. The method then proceeds to step 318.

Step 318: Calculate Time to Run

The time to run is then calculated based on the average flow rate measured in step 316, the mass of gas measured in step 312 is also used, along with the determination of the scaling factor E from the mass of gas measured in step 312 and in step 306.

The time to run value may be determined as the time to run to a particular fill level of the gas cylinder, i.e. the time until a predetermined quantity of gas remains. In one embodiment, this may be the time until the gas cylinder 12 is completely empty. Alternatively, the time to run may calculate the time until the cylinder is down to 10% of its full capacity. As further alternative, any desired predetermined level may be used at the end point for the time to run.

Step 320: Communicate Results

The time to run can be displayed in a number of ways. For example, the display 254 attached to the gas cylinder 12 or valve and regulator assembly 14 could display the time to run. In the alternative, time to run could be communicated remotely to a base station, a smartphone or other device located within wireless communication range of the gas cylinder and data module 250. If the time to run is short, e.g. only minutes remaining, or the capacity of the gas cylinder is low, a warning light may be displayed on the gas cylinder 12, for example, a warning light forming part of the display 258 or located on the guard 114. The method then proceeds to step 322.

Step 322: Delay

The method then waits for a predetermined time (e.g. 5 minutes) before moving back to step 308 to repeat the sequence for further measurements in a further measurement cycle m+1.

It is not necessary to keep the sensor assembly 200 operational at all times. To the contrary, it is beneficial to reduce power consumption by switching the sensor assembly 200 off when not in use. This prolongs the life of the battery 206.

The configuration of the drive circuit 204 enables the quartz crystal oscillator 202 to be restarted irrespective of the gas pressure in the gas cylinder 12. Therefore, the sensor assembly 200 can be shut down as and when required in order to save battery power.

Alternatively, if the flow rate is slow, or if it is desired to measure losses within the gas cylinder 12 due to, for example, leaks, then the time interval between $T_m$ and $T_{m+1}$ may be considerably greater; for example, of the order of minutes, hours or days.

The method then proceeds back to step 308 once the time period has expired.

Variations of the above embodiments will be apparent to the skilled person. The precise configuration of hardware and software components may differ and still fall within the scope of the present invention. The skilled person would be readily aware of alternative configurations which could be used.

For example, the above described embodiments have utilised a quartz crystal oscillator having a fundamental frequency of 32.768 kHz. However, crystals operating at alternative frequencies may be used. For example, quartz crystal oscillators operating at 60 kHz and 100 kHz may be used with the embodiments described above.

Further, whilst the above embodiment has been described with reference to the use of a quartz crystal oscillator, the skilled person would be readily aware of alternative piezoelectric materials which could also be used. For example, a non-exhaustive list may include crystal oscillators comprising: lithium tantalate, lithium niobate, lithium borate, berlinite, gallium arsenide, lithium tetraborate, aluminium phosphate, bismuth germanium oxide, polycrystalline zirconium titanate ceramics, high-alumina ceramics, silicon-zinc oxide composite, or dipotassium tartrate.

In addition, other sensors and methods for measuring mass of gas and flow rate may be used, or in combination. For example, a conventional flow meter may be used in conjunction with a quartz density sensor for mass measurement.

By way of further alternative, gas sensors different from piezoelectric oscillators could be used. A pressure sensor, solid state or a Bourdon gauge, could be used. Alternatively, the mass of the cylinder contents could be obtained by weighing and this, in conjunction with a conventional flow meter, could be used to determine mass at a later stage as the gas is consumed.

Embodiments of the present invention have been described with particular reference to the examples illustrated. While specific examples are shown in the drawings and are herein described in detail, it should be understood, however, that the drawings and detailed description are not intended to limit the invention to the particular form disclosed. It will be appreciated that variations and modifications may be made to the examples described within the scope of the present invention.

The invention claimed is:

1. A method of determining the predicted usage of gas from a gas cylinder assembly comprising a gas cylinder and a valve and regulator assembly, the method using a sensor assembly comprising a gas sensor and comprising the steps of:
   a) determining, using the gas sensor, the mass of gas in the gas cylinder at a time t;
   b) determining, at time t, the average measured flow rate of gas from the gas cylinder; and
   c) determining, at time t, the time remaining until the quantity of gas in the gas cylinder reaches a predetermined level, the time remaining being determined from the mass of gas in the gas cylinder at time t, the average measured flow rate of gas from the gas cylinder as determined at time t, and a predetermined scaling factor selected in dependence upon the proportion of gas remaining in the gas cylinder at time t;
   wherein the gas sensor comprises a piezoelectric oscillator immersed in the gas within the gas cylinder, and the sensor assembly comprises a drive circuit for driving the piezoelectric oscillator, and step a) comprises:
   d) driving, by means of the drive circuit, the piezoelectric oscillator such that the piezoelectric oscillator resonates at a resonant frequency; and
   e) measuring the resonant frequency of the piezoelectric oscillator at time t; and
   f) determining, from the resonant frequency, the mass of the gas within the gas cylinder at time t.

2. A method according to claim 1, wherein step b) comprises determining the average measured flow rate of gas from either:
   g) n previous measurements of the flow rate of the gas, where n>1; or
   h) where there are fewer than n previous measurements of the flow rate of the gas, a predetermined starting flow rate.

3. A method according to claim 2, wherein each of said previous measurements of the measured flow rate of the gas is calculated from the difference between the resonant frequency of the piezoelectric oscillator at a first time and the resonant frequency of the piezoelectric oscillator at a second, earlier, time.

4. A method according to claim 1, wherein the method further comprises, prior to step a):
   i) determining the mass of gas in the gas cylinder when the gas cylinder is full, and wherein step c) further comprises:
   j) determining the proportion of gas remaining in the gas cylinder at time t from the mass of gas in the gas cylinder when full and the mass of the gas in the gas cylinder at time t.

5. A method according to claim 1, wherein the predetermined scaling factor is selected from a look up table.

6. A method according to claim 1, wherein the time remaining until a predetermined quantity of gas remains in the gas cylinder is calculated based on a function comprising a constant base flow rate and the average measured flow rate of gas.

7. A method according to claim 6, wherein the relative weight of the constant base flow rate component to the average measured flow rate component in the calculation is dependent upon the predetermined scaling factor.

8. A method according to claim 6, wherein the constant base flow rate comprises a predetermined fixed value.

9. A method according to claim 6, wherein the constant base flow rate is selected by a user.

10. A method according to claim 6, wherein the constant base flow rate is selected from a plurality of constant base flow rates stored in a look up table.

11. A method according to claim 6, further comprising the step of:
   k) updating the constant base flow rate based on a measurement of the actual flow rate.

12. A method according to claim 1, wherein the predetermined level of the quantity of gas in the gas cylinder is substantially zero.

13. A sensor assembly comprising a processor and a gas sensor, the sensor assembly being configured to carry out the steps of claim 1.

14. A sensor assembly according to claim 13, further comprising a display arranged to be located on the gas cylinder and valve and regulator assembly.

15. A sensor assembly according to claim 13, further comprising wireless communication means for communicating with electronic devices.

16. A gas cylinder assembly comprising a valve and regulator assembly and the sensor assembly of claim 13.

* * * * *